United States Patent [19]

Payton

[11] Patent Number: 4,660,555

[45] Date of Patent: Apr. 28, 1987

[54] OXYGEN DELIVERY AND ADMINISTRATION SYSTEM

[76] Inventor: Hugh W. Payton, 36 S. Main St., Jeffersonville, Ohio 43128

[21] Appl. No.: 798,519

[22] Filed: Nov. 15, 1985

Related U.S. Application Data

[63] Continuation-in-part of Ser. No. 653,820, Sep. 21, 1984, which is a continuation-in-part of Ser. No. 586,455, Mar. 5, 1984, abandoned.

[51] Int. Cl.$^4$ .............................................. A61M 16/00
[52] U.S. Cl. ...................... 128/207.18; 128/DIG. 26; 604/94; 604/275
[58] Field of Search ...................... 128/207.18, 203.22, 128/203.23, 206.11, 151, 152, DIG. 26; 604/94, 275

[56] References Cited

U.S. PATENT DOCUMENTS

| | | | |
|---|---|---|---|
| 1,060,665 | 5/1913 | Bell . | |
| 1,806,453 | 5/1931 | Gibson | 128/203.22 |
| 2,135,052 | 11/1938 | Rose | 604/275 |
| 2,168,705 | 8/1939 | Francisco et al. . | |
| 2,191,016 | 2/1940 | Hoffman | 128/203.23 |
| 2,259,817 | 10/1941 | Hawkins | 128/206 |
| 2,448,803 | 9/1948 | Hunter | 604/275 |
| 2,590,006 | 3/1952 | Gordon | 128/206 |
| 2,693,800 | 11/1954 | Caldwell | 128/206 |
| 3,288,136 | 11/1966 | Lund | 128/133 |
| 3,500,823 | 3/1970 | Richardson et al. | 128/2.06 |
| 3,782,388 | 1/1974 | Page | 128/348 |
| 3,802,431 | 4/1974 | Farr | 128/206 |
| 3,915,173 | 10/1975 | Brekke | 128/351 |
| 4,025,015 | 5/1977 | Kolic | 248/205 |
| 4,122,857 | 10/1978 | Haerr | 128/348 |
| 4,156,426 | 5/1979 | Gold | 128/205 |
| 4,170,995 | 10/1979 | Levine et al. | 128/346 |
| 4,209,020 | 6/1980 | Nielsen | 128/640 |
| 4,273,124 | 6/1981 | Zimmerman | 128/245 |
| 4,282,871 | 8/1981 | Chodorow et al. | 128/207.18 |
| 4,300,545 | 11/1981 | Goodnow et al. | 604/275 |
| 4,363,323 | 12/1982 | Geiss | 604/281 |
| 4,406,283 | 9/1983 | Bir | 128/207.18 |
| 4,418,697 | 12/1983 | Tama | 128/640 |
| 4,535,767 | 8/1985 | Tiep et al. | 128/207.18 |

FOREIGN PATENT DOCUMENTS

| | | |
|---|---|---|
| 166171 | 3/1905 | Fed. Rep. of Germany ........................ 128/207.18 |
| 1124404 | 10/1951 | France . |

Primary Examiner—Henry J. Recla
Attorney, Agent, or Firm—Biebel, French & Nauman

[57] ABSTRACT

A system for supplying supplemental oxygen to a patient includes a nosepiece and an oxygen tube holder. The nosepiece has a conical section with a truncated tip and a flexible annular skirt and is formed with a primary axial oxygen passageway and a pair of lateral secondary oxygen passages which lead from the primary passageway to outlets on the conical surface. Optionally, an additional pair of passageways lead through the nosepiece from a position outwardly of the skirt into the axial passageway. In alternative forms, the nosepiece has a tear-away skirt portion to permit the diameter to be changed to accommodate the individual, and has external air passageways formed as recesses on the conical surface. The tube holder is arcuate and is adapted to be mounted on an EKG electrode-type patch on a cheek prominence and supports an oxygen delivery tube to the nosepiece. The electrode post is received within a curved slot formed in the holder base. Grippers on the base hold the oxygen tube in a relation conforming to the curvature of the base.

5 Claims, 12 Drawing Figures

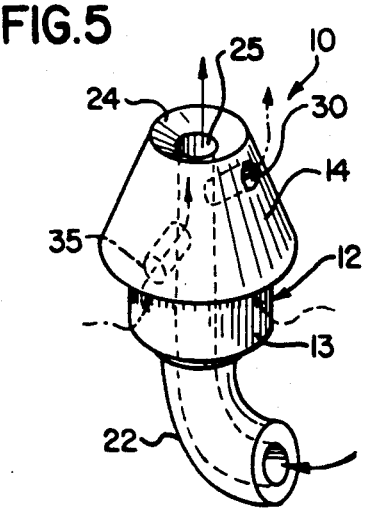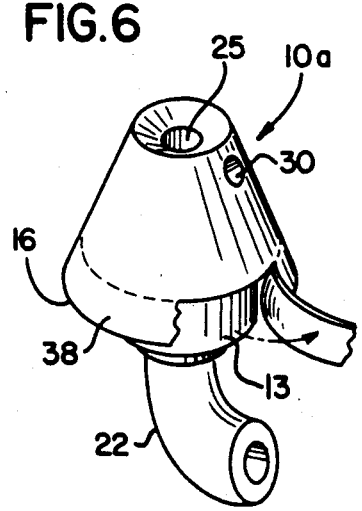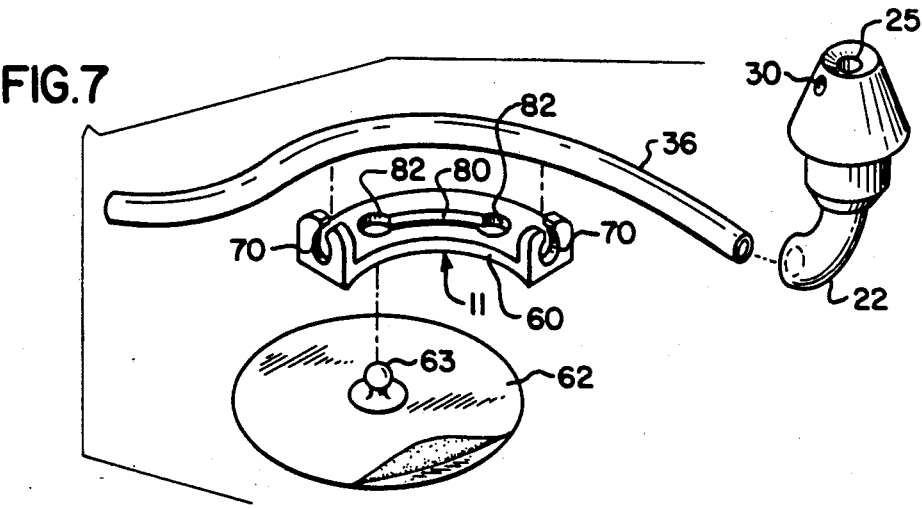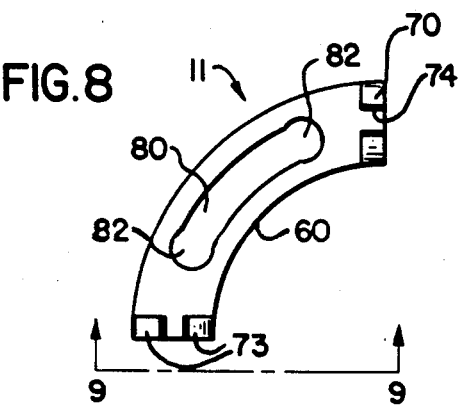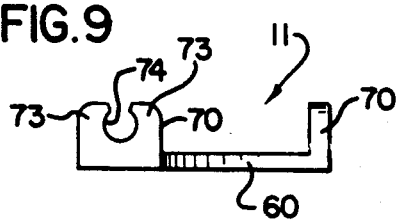

OXYGEN DELIVERY AND ADMINISTRATION SYSTEM

RELATED APPLICATION

This application is a continuation-in-part of application of Ser. No. 653,820 filed Sept. 21, 1984, which is a continuation-in-part of application Ser. No. 586,455 filed Mar. 5, 1984, now abandoned.

BACKGROUND OF THE INVENTION

This application relates to apparatus for applying supplemental oxygen to a patient.

The dual prong nasal cannula is in generally standard use today. It can become quite uncomfortable for a patient. The most commonly used arrangement includes a dual prong nosepiece which is centered in a loop of vinyl tubing. The nosepiece openings are inserted in the nose with the tubing tucked behind the ears. A slide adjustment may be used to draw it tight beneath the chin. By the third or fourth day of its use, irritation of the skin areas in contact with the cannula has begun. By the fifth day, the majority of patients have begun to use tissues and the like to relieve the soreness under the nose and around the ears. This soreness and irritation is often due to abrasion which is often caused by movement of the tight fitting tube and to the accumulation of moisture between the skin and the vinyl under the nose. In men, growth of the beard can further aggravate the situation.

The comfort of the patient becomes more critical, both to the patient and to the professionals attending the patient when the patient is also fitted with a naso-gastric or Levine tube. Now the nose becomes a fairly cluttered access route, and adhesive tape is often used, by application to the face, to get all the tubes to remain in place.

In cases where supplemental oxygen is required, a patient may suffer from "free floating anxiety" as a result of reduced blood oxygen. Such patient may believe something is wrong but cannot quite identify the problem, and may not be thinking clearly. Often such patients have feelings of claustrophobia and may attempt to remove the cannula despite the fact that doing so may adversely affect the patient's condition. It is not uncommon to find the tubing disconnected and on the floor. Further, patient non-compliance or lack of cooperation may necessitate the use of some more expensive or aggressive means of oxygen administration, including face masks or catheters.

Studies have indicated that unilateral oxygen administration, as shown by the system described and claimed in the copending application Ser. No. 653,820, may be at least as effective in the administration of supplemental oxygen as in the case where oxygen is admitted to both nares simultaneously.

To an increasing extent, supplemental oxygen is used on an outpatient basis, such as in a home. Under such conditions, the cosmetics of the oxygen applicating apparatus can be important, and the commonly-used dual prong cannula can make a person feel conspicuous.

SUMMARY OF THE INVENTION

The present invention is directed to improved apparatus for the delivery of supplemental oxygen to a patient, and more particularly provides such apparatus which may be used with the system described in the above-identified copending application Ser. No. 653,820. A particular object of this invention is the provision of an improved nosepiece formed of soft elastomer material for the delivery of supplemental oxygen. The nosepiece has the general form or shape of a cone. It may have an annular skirt at the base formed with a thin wall section which permits the nosepiece to be inserted comfortably within and to conform to the nasal cavity.

The nosepiece is formed with an axial or central oxygen passageway therethrough, leading from an inlet and terminating at the apex. Preferably, the conical section of the nosepiece is truncated, with the oxygen passageway opening centrally of the truncated portion. There may be provided one or more supplemental oxygen passageways which lead from the main or axial passageway and terminate at the conical surface, forward or inward of the skirt, in order to provide for the delivery of oxygen in the event of plugging or stoppage of the main passageway. The truncated end of the conical portion is preferably formed with a reverse conical surface surrounding the main oxygen outlet, to provide a soft protuberance which tends to prevent membrane irritation when the nosepiece is inserted.

The nosepiece further may optionally include one or more auxiliary passageways through which the patient may breath or inhale outside air, to alleviate feelings of claustrophobia or suffocation. Such optional or auxiliary passageways may open into the main axial passageway at their inner ends to receive outside or room air at the body at a position axially outwardly or below the skirt. Alternatively, auxiliary grooves or passageways may be formed in the outer occluding surface of the nose cone for admission of supplemental air.

An improved oxygen delivery tube retainer or holder is also disclosed and forms a part of this invention. The holder is formed as a base having a generally arcuate shape, and having a size which is comfortable for support on a skin patch in accordance with the teachings of the copending application. The oxygen tube holder is provided with spaced tube grippers or fingers which support a section of the tube in a curved configuration conforming generally to the arcuate curvature of the holder. The holder thus preforms the tube and permits one end of the tube to exit naturally to a nare with the other end of the tube exiting naturally along the side of the face, such as over the ear or to a bedsheet clip.

The tube holder is adopted to be mounted on a support patch having a central retaining electrode or button. The holder has an arcuate slot which permits it to be moved along the button, for more readily adjusting the curvature of the oxygen hose to a natural position.

A particular advantage of the oxygen support and delivery apparatus of the present invention is that it is adapted to be used on either side of the face. The holder is reversible so that it may be supported on a skin patch at a cheek prominence on either side of the face. The grippers preform the tube in a natural curvature and eliminate the necessity of using a stiffened section of oxygen delivery tube, or a tube with a positional memory. Thus, conventional soft plastic oxygen delivery tubing may be used throughout.

The employment of conventional EKG electrode-type skin patches has the advantage of providing a sturdy central mount for supporting the tube holder while providing free pivotal movement of the holder about the axis of the electrode.

It is accordingly an important object of this invention to provide a nosepiece for the application of oxygen in the form of an applicator of truncated conical shape adapted to be inserted within a nostril cavity for substantially occluding the cavity and having an oxygen passageway therethrough for delivery of oxygen to a patient requiring supplemental oxygen.

A further object of the invention is the provision of a nosepiece formed of soft, pliable elastomeric material and a skirt and truncated inner end of reverse curvature with an axial oxygen passageway centrally therethrough. The nosepiece may also have supplemental air or oxygen passageways opening into the axial passageway or one or more internal or external "breath-through" passages to relieve feelings of claustrophobia.

A still further object is the provision of a curved or arcuate oxygen tube holder adapted to be supported on a skin patch, such as an EKG-type patch, with oxygen tube gripping members at the arcuate ends thereof for supporting a section of oxygen tube in a curved preformed manner coinciding substantially with the shape of the holder.

A further object of the invention is the provision of a curved tube holder for supporting an oxygen tube on the cheek of a patient requiring supplemental oxygen, which holder is adopted to be supported and carried on an EKG-electrode patch and which is curved to provide lateral support for the tube at two locations while holding the tube in a natural curved condition.

These and other objects and advantages of the invention will be apparent from the following description, accompanying drawings and the appended claims.

BRIEF DESCRIPTION OF THE DRAWINGS

FIG. 5 is a perspective view of the nosepiece with arrows showing the direction of airflow and oxygen flow thereto;

FIG. 6 is a view similar to FIG. 5, but showing a modified embodiment of the nosepiece with a tear-away strip;

FIG. 7 is an exploded view showing the improved oxygen tube holder of this invention, and illustrating the position of the oxygen tube and the EKG-type skin patch support;

FIG. 8 is a plan view of the holder of FIG. 7;

FIG. 9 is an end elevation of the improved holder taken generally along the line 9—9 of FIG. 8; and FIGS. 10-12 illustrate a further modified form of the nosepiece in which FIG. 10 is a perspective view;

FIG. 11 is an enlarged end view; and

FIG. 12 is a sectional view along line 12—12 of FIG. 11.

DESCRIPTION OF THE PREFERRED EMBODIMENTS

Figure 1:
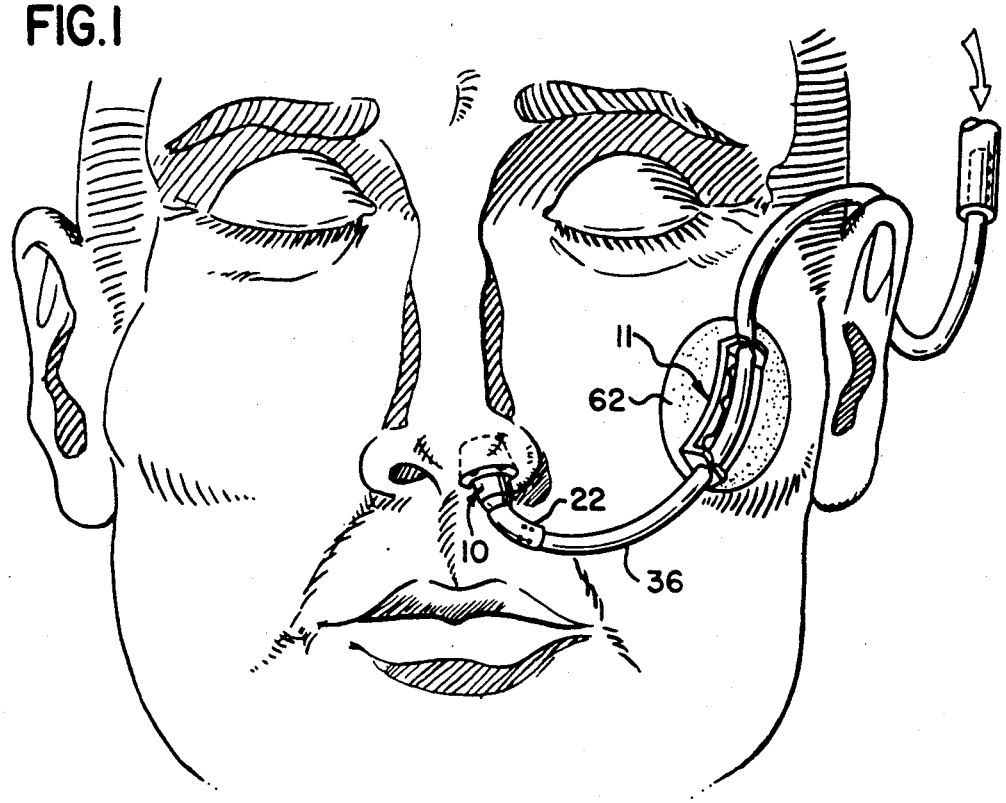
FIG. 1 is a frontal view of a patient using a supplemental oxygen system in accordance with this invention.
Figure 2:
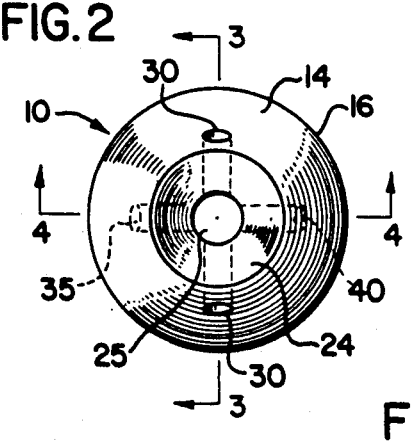
FIG. 2 is an enlarged frontal view of the improved nosepiece of this invention.

Referring to the figures of the drawing, the improved oxygen applicator system for the delivery of supplemental oxygen to a nostril of a patient includes an improved nosepiece 10 and an improved oxygen tube holder 11.

Referring to FIGS. 2-5, the nosepiece 10 is formed by molding a body 12 of relatively soft elastomeric material, such as silicone rubber, or FDA grade vinyl. The body 12 has an outwardly or rearwardly extending cylindrical section 13 and a forward section 14 formed generally in the shape of a cone. The cone section 14 has a truncated inner end 15 and an outwardly tapered annular skirt 16. The skirt 16 forms at its outer surface a continuation of the outside conical surface 17 of the section 14 and extends rearwardly in partially overlying relation to the cyindrical section 13. The skirt 16 has a wall thickness, at its base, which permits the skirt 16 to be readily and easily deflected, to conform generally to the configuration of the surrounding nasal membrane surfaces. The shape or taper of the conical surface 17 may be approximately 15°-30° from the central axis, although the precise slope is not critical. The maximum diameter of the nosepiece 10, at the skirt 16, is chosen so as to comfortably fit within the nasal cavity of a patient, as shown in FIG. 1.

Figure 3:
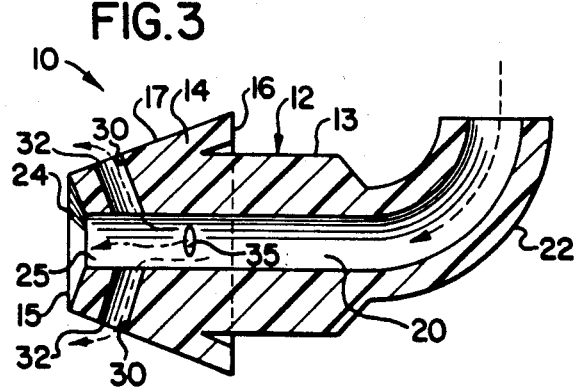
FIG. 3 is a transverse section taken generally along the line 3—3 of FIG. 2.

The body 12 defines a primary generally axially-extending oxygen passageway 20 therethrough, leading from a curved inlet tube-like portion 22 extending from the body 12 and through the conical section 14, and opening centrally at the truncated end 15. The truncated end 15 is formed with an inwardly tapering or reverse conical surface 24, leading to a central oxygen outlet 25 at the terminal end of the passageway 20. The improved nosepiece of the embodient of FIGS. 2-5 also includes one or more supplemental, laterally directed passages 30. As shown in FIG. 3, a pair of the passages 30 extend laterally from the axial or main passageway 20 and terminate at outlets 32 on the surface 17 of the conical section 14 adjacent the truncated end 15. The purpose of the supplemental passage is to ensure a free and adequate supply of oxygen in the event one of the other oxygen passageways becomes plugged or stopped. Thus, if the primary central oxygen outlet 25 should become temporarily stopped with mucous or the like, oxygen can still be delivered through the opposed pair of lateral passages 30 and the outlets 32. The arrangement permits the delivery of an adequate quantity of oxygen, in the range of eight liters per minute, as presently applied by the two prong cannula method.

Figure 4:
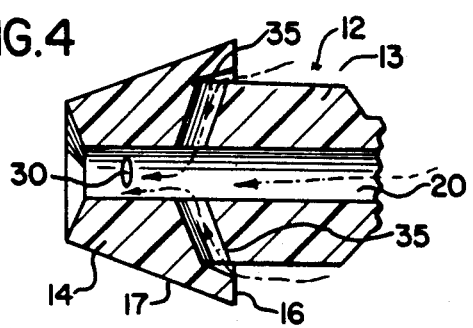
FIG. 4 is another transverse and partially broken away section taken generally the line 4—4 of FIG. 2.

In certain instances, a patient may suffer the feeling of claustrophobia, which feeling may be relieved by permitting the patient to breath outside air through the nosepiece. For this purpose, a second pair of lateral passageways 35 may be provided leading through the cylindrical section 13 from a position underlying the skirt 16 into the central passageway 20. As shown in FIG. 4, a diametrically opposed pair of such passageways are provided which permit the patient to breath through the nosepiece by drawing room air inwardly through the supplemental lateral passages 40 and into the axial passage 20 to supplement the oxygen. The supplemental passages 35 may be omitted where the patient does not feel the necessity for breathing through the nosepiece.

The outer curved tube-like portion 22 is proportioned to slip over the outside surface of an oxygen delivery tube 36, as shown in FIGS. 1 and 7. The curvature of the portion 22 permits the tube 36 to be carried off from the side of the face in a pleasing and attractive manner.

A modified form of the nosepiece 10a is shown in FIG. 6 in which an extended skirt or section 38 of the skirt 16 is connected to the main body of the skirt by a weakened tear joint 39. The annular skirt section 38 may be removed by pulling and separating the same at the weakened joint 39 and thereby may be removed in the manner of a tear strip, to provide a nosepiece of more universal application. Where the nares are large the full skirt 35 would remain in place, but for a smaller person, or a child, the major portion of the skirt may be removed, thereby effectively decreasing the overall diameter of the nosepiece.

Figure 10:
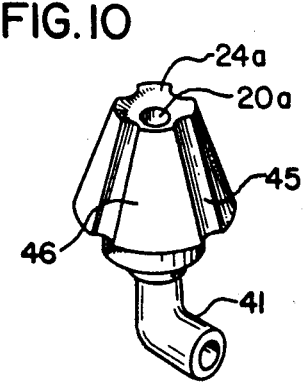
Figure 11:
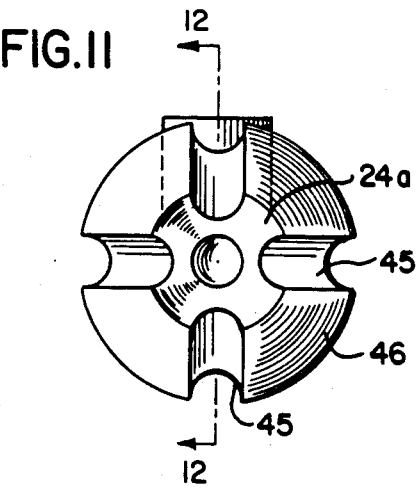
Figure 12:
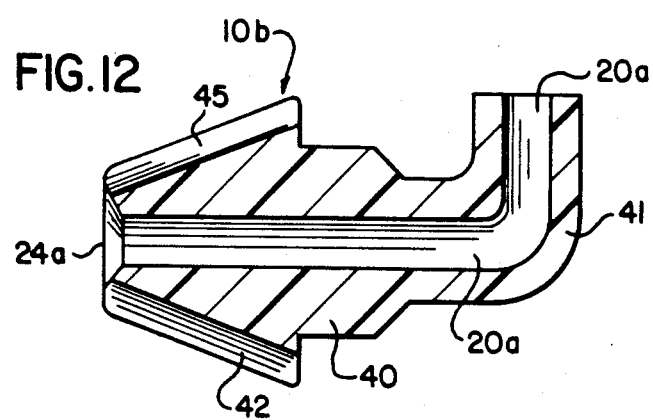

In the modifications of the preferred embodiment of FIGS. 10–12, the nosepiece 10b is formed with a molded body 40 having, at its outer end, a right angle elbow lead-in section 41 defining the central passageway 20a therethrough. The forward enlarged end 42 of the improved nosepiece 10b has a generally conical outer surface as in the preceding embodiments. The lead-in elbow 41 is also proportional to slip over an oxygen delivery tube 36.

Thus, the enlarged end 42 has a frustoconical shape which is formed with the reverse conical surface 24a at the nose thereof, corresponding to the surface 24 of the preceding embodiments. The central oxygen passageway 20a exits centrally of the end defined at the surface 24a.

Means for providing auxiliary air, to alleviate feelings of claustrophobia, take the form of a plurality of external semi-cylindrically shaped grooves or passageways 45 formed in the outer surface of the conical end 42. The passageways 45 lead from the wide or large end of the conical surface 46 to the small end and permit the ingress of outside air. They perform the same purpose as the passageways 35 of the preceding embodiment. While four such semi-cylindrical grooves 45 are shown in the improved nosepiece 10b, more or less may be employed as determined desirable for the comfort and well being of the patient.

The nosepiece 10b is preferably molded from a medical grade vinyl with a durometer of between 30 and 45, although other materials may be used, such as silicone rubber.

A further aspect of the invention provides an improved support 11 for the oxygen delivery tube 50. As shown in FIGS. 7–9, the support has an arcuately shaped base 60 of a size for comfortable support on or by an electrode type skin patch 62, on a non-hairy cheek prominence or the like as disclosed in copending application Ser. No. 653,820. The skin patch 62 is conveniently provided with a generally centrally located upstanding metallic post 63, such as an electrode post commonly used for EKG applications. Preferably, relatively small patches may be used, such as those commonly available for use with pediatric patients.

The support base 60 is formed with a central portion of generally constant thickness and is molded in a generally arcuate shape, such as 90°, as shown in FIG. 8. The base 60 has formed at each end a pair of tube grippers 70. The grippers 70 are formed as upstanding ends of the base, as viewed in elevation in FIG. 9, and comprise a pair of opposed fingers 73 which define a slot 74 which is narrower at the entrance. The slot is proportioned to receive the oxygen tube 36 therethrough, simply by pressing the same in the slot. The first pair of transversely-spaced tube grippers defined by the finger 73 is positioned at one arcuate end of the base while a second pair of identical tube grippers are formed at the opposite end of the base 60. The tube gripper pairs combine to support the oxygen tube 36 therebetween in a curved relation, in general conformity with the curve or shape of the base 60, thereby setting a preformed curvature to the tube.

The means on the base 60 for receiving the electrode post 63 includes an arcuate slot 80, the major portion of which has a transverse width less than the maximum width of the post 63. However, at least one end of the slot 80 (and preferably both ends of the slot) are enlarged as indicated at 82 to receive the post 63 therethrough for positioning along the slot. It can be seen that the support base is fully reversible and may readily be secured at either cheek prominence, to an electrode-type skin patch.

In use, the base 60 is positioned with its curvature complementing the natural curvature of the oxygen tube from the nose cone or nosepiece, as shown in FIG. 1, so that the length of tube 36 between the base 60 and the nosepiece 10 continues with a curvature as established by the base 60, simply by sliding the appropriate amount of oxygen tube 36 through the base, and positioning the support 11 on its post 63, so that there is little or no stress on the nosepiece 10. The base 60 remains free to pivot about the post 63 of the patch 62 to assure a natural position with a minimum of stress on the delivery end of the tube 36. It has been found that the flexible plastic oxygen tube 36 will reliably remain in place, with the nosepiece 10 inserted, without the need for supplemental stiffening or preset in this region.

Preferably, the tube 36 is supported at a second non-hairy prominence in the manner described in copending application Ser. No. 653,820. For this purpose, the tube may be carried behind the ear, as shown in FIG. 1, and attached by a second attachment to the mastoid area in the manner described in the copending application, utilizing a skin patch and split tube clamp arrangement or utilizing another support 11.

It will thus be seen that this application provides apparatus which is particularly useful for the unilateral application of supplemental oxygen to a patient requiring supplemental oxygen. The nosepiece, having a forward portion of generally conical shape with a flared skirt portion and a truncated tip, permits the ready insertion and the comfortable accommodation in a nasal cavity, with the inlet curved end 22 or 42 extending outwardly for attachment over an oxygen delivery tube. The lateral passageways 30 and the central opening 25 provide independent outlets for oxygen, assuring the delivery of an adequate supply of oxygen in case one becomes plugged. In addition, the auxiliary and optional air inlets 35 or 45, permit ingress of outside air, where desired, permitting the patient to breath "through" the nosepiece.

The curved tube holder 11 has particular advantage of simplicity and low cost. It may be readily adjusted by sliding the same along the patch 62, to position the electrode 63 within the slot 80, as is desired, so as to locate the section of the oxygen tube 36 leading to the nosepiece, and accommodate variations in facial contours and the like. The support base or holder is readily removable and insertable by aligning one or the other of the enlarged ends 82 with the electrode 63. The oxygen tube 50 can readily be attached simply by pressing the same between the opposed fingers or grippers 73 which define the slots 72, as illustrated in FIG. 7. The oxygen tube supports may be used on either side of the face since they are fully reversible in position.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. In an oxygen applicator system for the delivery of supplemental oxygen to a nostril of a patient, the improvement comprising:

a cone-shaped nosepiece formed of soft elastomer having a truncated inner end and a depending surrounding outwardly-tapered skirt, said nosepiece at the truncated end thereof formed with a reverse conical surface, the dimension of said skirt at the base thereof being proportioned to be received comfortably in the nasal cavity, said skirt having a wall thickness which permits it to readily conform to surrounding nasal membrane surfaces, means in said nosepiece defining a central oxygen inlet at the base thereof and extending axially therethrough and opening at said truncated end forming an axial oxygen passageway, and said nosepiece further having a plurality of auxiliary air passages leading to said axial passageway.

2. In an oxygen applicator system for the delivery of supplemental oxygen to the nostril of a patient, the improvement comprising:

a cone-shaped nosepiece formed of soft elastomer having a truncated inner end and a depending surrounding outwardly-tapered skirt, the dimension of said skirt at the base thereof being proportioned to be received comfortably in the nasal cavity, said skirt having an annular weak zone to permit an outer strip of said skirt to be pulled off of the remaining skirt by separation at said weak zone to decrease the diameter of said nosepiece at the base thereof, means in said nosepiece defining a central oxygen inlet at the base thereof and extending axially therethrough and opening at said truncated end forming an axial oxygen passageway, and said nosepiece further having a plurality of auxiliary air passages leading to said axial passageway.

3. The system of claim 1 in which said auxiliary air passages are formed on an outer surface of said nosepiece.

4. The system of claim 1 in which said auxiliary air passages are formed internally in said nosepiece and lead from a position under said depending skirt into said axial oxygen passageway.

5. The system of claim 1 further comprising auxiliary oxygen passageways leading laterally from said axial passageway and terminating on an outer surface of said nosepiece spaced from said reverse conical surface.

* * * * *